United States Patent [19]

Müller

[11] 4,014,326
[45] Mar. 29, 1977

[54] RESPIRATOR SYSTEM
[75] Inventor: Robert Müller, Taby, Sweden
[73] Assignee: Cameco AB, Enebyberg, Sweden
[22] Filed: Apr. 21, 1976
[21] Appl. No.: 678,861
[30] Foreign Application Priority Data
   Apr. 30, 1975 Sweden .............................. 7505099
[52] U.S. Cl. .......................... 128/145.6; 128/145.7; 128/DIG. 17; 128/142.2
[51] Int. Cl.² ......................................... A61M 16/00
[58] Field of Search ......... 128/145.5, 145.6, 145.8, 128/142.2, 188, DIG. 17

[56] References Cited
UNITED STATES PATENTS 3,316,902  5/1967  Winchel et al. ............ 128/DIG. 17
3,527,555  9/1970  Schreiber ...................... 128/145.8

Primary Examiner—Robert W. Michell
Assistant Examiner—Henry J. Recla
Attorney, Agent, or Firm—Laff, Whitesel & Rockman

[57] ABSTRACT

A compact respirator system for use either connected to stationary outlets for breathing gas or connected as a portable unit to a tube of breathing gas. A breathing bladder and a valve block form a unit that may be disposed either with the breathing bladder in a pressure chamber for conventional respiratory operation or with the breathing bladder removed from the pressure chamber for manual actuation. A pulse transmitter actuates a pressure pulse generator for providing the pressure chamber with intermittent pulses for compressing and expanding, respectively, the breathing bladder for said conventional respiratory operation. An automatic valve keeps open a pilot pressure channel to an expiratory valve forming a portion of a pilot valve, which latter also includes a patient-triggered valve for initiating rapid breathing assistance if the patient shows signs of beginning to breathe spontaneously.

7 Claims, 7 Drawing Figures

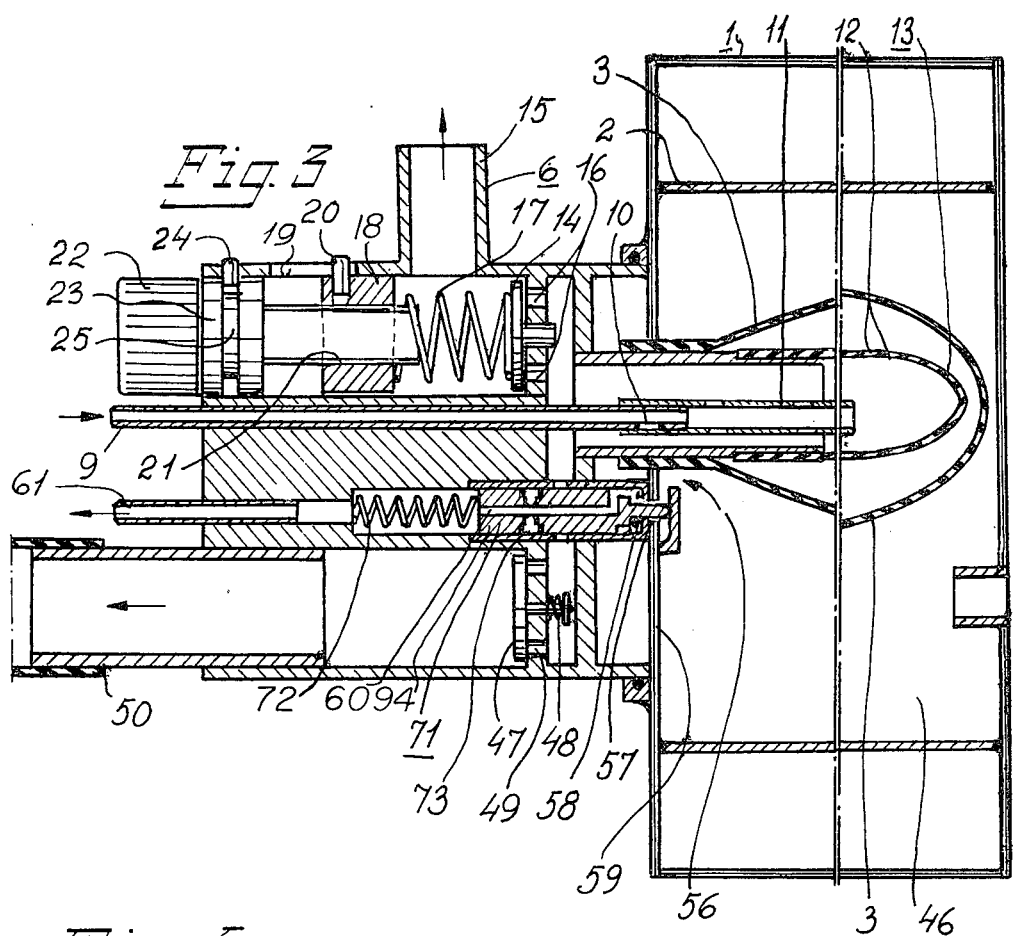
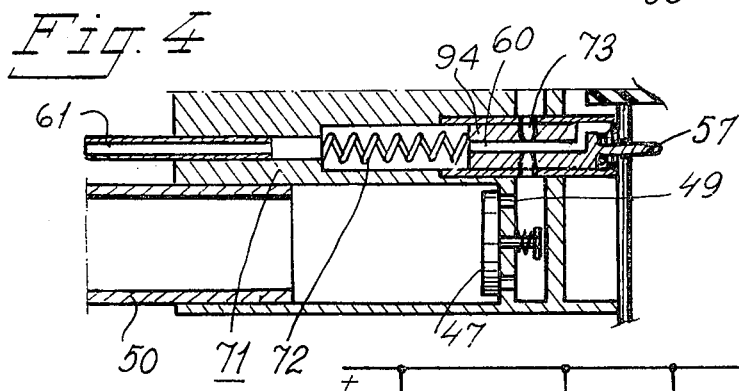
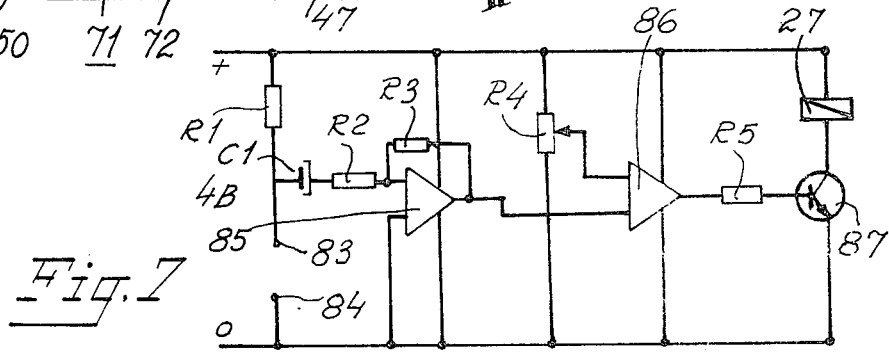

RESPIRATOR SYSTEM

BACKGROUND OF THE INVENTION

1. Field of the Invention

This invention refers to a compact respirator system which may be used either connected to stationary outlets of breathing gas or connected as a portable unit to a tube of breathing gas so as to be able to be moved along with a patient lying on a stretcher or a bed.

2. Description of the Prior Art

A number of respirator systems are known and have been in use for many years. However, these known systems have certain disadvantages, such as requiring comparatively large space and thus being unwieldly when being moved. Furthermore, the patient-triggered devices included in some of them, i.e. devices for quickly supplying breathing gas from the respirator to the patient when the patient shows indications of beginning to breath spontaneously, either require too large triggering volume or else they require too high negative pressure in order to give the patient breathing assistance sufficiently rapidly. Hence, the known patient-triggered devices have too great delays.

SUMMARY OF THE INVENTION

The present invention has the object of eliminating these disadvantages by providing a compact respirator system whose respirator may be utilized either connected to permanent breathing gas supply conduits or connected to a tube containing breathing gas, with the respirator having so small dimensions that in the last-mentioned case it for example may be placed on a bed in which a newly operated patient is lying and then together with the tube of breathing gas can ride along with the bed and the patient lying in the latter to a supervisory place, whereafter, when the patient is transferred to a room in a ward, the respirator may be connected to a permanent conduit for supplying breathing gas. Furthermore, the invention has the object of providing a respirator system with a patient-triggered device which is triggered at a high rate after having been initiated by a very weak spontaneous reaction of a patient and which then causes the patient immediately to receive breathing help to supplement this spontaneous reaction. Breathing help of this type is extremely important in connection with rehabilitating patients, as it may be difficult to relieve them from the breathing help that they are given by the respirator. By means of a patient-triggered device it is possible to enable the patient initially only to have to perform a small portion of the breathing work, whereafter this portion can be increased progressively. Another object of the invention is to provide an automatic valve which, when the above-mentioned valve block is introduced in the pressure chamber, supplies pressure to an expiratory valve, whereby it is possible to avoid the risk that a pressure that is dangerous to the patient may be created if the supply of breathing gas to the breathing bladder turns out to be greater than necessary.

The respirator system of the type mentioned by way of introduction has a valve block detachably connected to a pressure chamber and comprising an automatic valve which interconnects the pressure chamber and a pilot valve, which latter includes an expiratory valve. Said automatic valve includes a spring-loaded pin which remains depressed when the valve block is connected to the pressure chamber so as to keep open a pilot pressure channel through which atmospheric air is supplied from the pressure chamber to the expiratory valve, simultaneously with breathing gas being conveyed from the breathing bladder to the patient, whereas said pin is extended when the valve block is disconnected from the pressure chamber and in this case keeps said pilot pressure channel under pressure from the interior of the breathing bladder and simultaneously enables breathing gas to be supplied to the patient by manual actuation of the breathing bladder. The respirator system of the invention may to advantage comprise a patient-triggered valve with a diaphragm which is extremely mobile and a hot-wire transmitter for operating the pressure pulse transmitter substantially without any time delay as the result of a spontaneous inhaling reaction of the patient so that the pressure chamber is immediately set under pressure and hence by means of its pressure on the breathing bladder causes breathing gas to be supplied to the lungs of the patient. In addition to the expiratory valve, the patient-triggered valve may also be included as a portion of the pilot valve. The expiratory valve may appropriately comprise a valve bladder which when subjected to pressurized gas from the pressure chamber or breathing gas from the breathing bladder is urged against a valve seat in the pilot valve, and a spring-loaded displaceable pressure plate may be disposed in the valve bladder for cooperating with the valve bladder and said valve seat in such manner that a predetermined pressure is retained in the lungs of the patient after expiration has been performed. A conduit disposed in the pressure pulse generator for supplying atmospheric air under comparatively high pressure may be connected to an injector which on one hand communicates with the pressure chamber and on the other hand communicates with the surrounding atmosphere through apertures in an injector block, whereby a predetermined maximum pressure of the pressure chamber cannot be exceeded. Pressure relief of the pressure chamber will then be carried out by means of said apertures. The compact design of the respirator system of the invention is achieved primarily as the result of the longitudinal partition of the pressure chamber having oval cross-section.

BRIEF DESCRIPTION OF THE DRAWINGS

The invention will be described more specifically in the following with reference to the accompanying drawings, in which FIG. 3 is an enlarged view of a valve block included in the respirator system of the invention and being connected to the pressure chamber with its enclosed breathing bladder, wherein an automatic valve for pilot pressure is shown in one of its end positions, FIG. 4 is a view of the automatic valve according to FIG. 3 in its opposite end position, FIG. 7 is a circuit diagram of the patient-triggered electronic circuit of the invention serving as an example. The same reference numerals have been utilized in the various figures wherever possible.

DESCRIPTION OF THE PREFERRED EMBODIMENT

Figure 1:
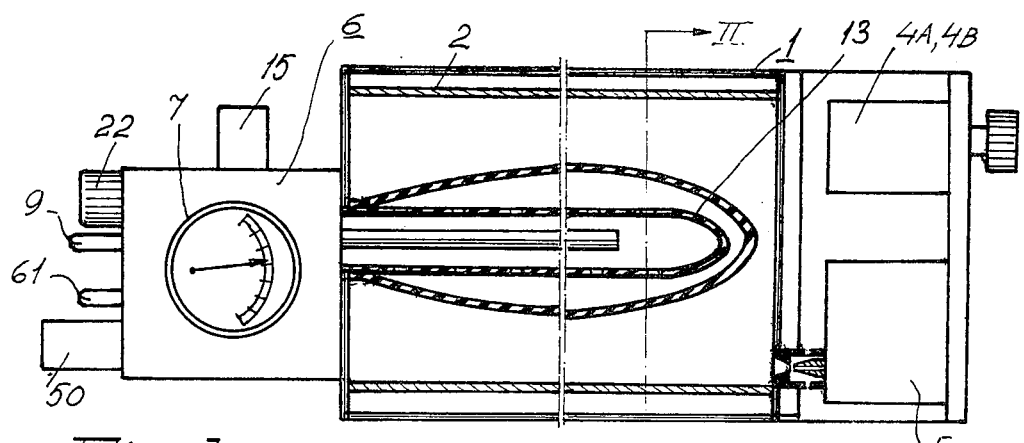
FIG. 1 shows a view of part of the respirator system of the invention with the components that are connected most closely to the breathing bladder.
Figure 2:
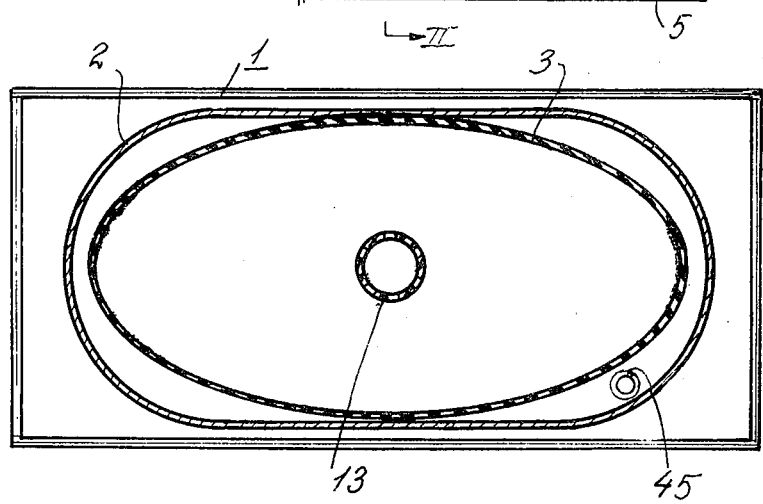
FIG. 2 is a sectional view of the pressure chamber of the respirator of the invention taken along the line II—II of FIG. 1.

FIG. 1 diagrammatically shows an example of the design of the breathing gas supply portion of the respirator system in accordance with the invention. Into an external casing 1 are built on one hand an internal casing 2, which to advantage may be oval in cross-section, as can be seen in FIG. 2, and which surrounds a breathing bladder 3, and on the other hand an electronic unit 4A, 4B, which comprises an electronic pulse transmitter 4A and a trigger circuit 4B, and finally a pressure pulse generator 5. These components will be described more specifically below. The breathing bladder 3 is secured in casing 1 by means of a valve block 6 which may be provided with a manometer 7 showing the pressure in conduit 50 which extends from valve block 6 to the lungs of the patient and which will be described more specifically below.

As may be seen in FIG. 3, which shows valve block 6 and breathing bladder 3 in the inner casing 2 more in detail, breathing gas, for instance oxygen or anaesthetic gas, can be supplied to the breathing bladder 3 through a conduit 9 and may be introduced into the bladder 3 through an aperture 10 in an elongated sheath 11 consisting of resilient material which operates like a check valve with regard to the supplied breathing gas so that said gas can pass through the apertures 10 but is prevented from being returned from sheath 11 in the opposite direction in conduit 9. (In order to simplify the drawing, casing 1 and its contents have been cut short in FIGS. 1 and 3, respectively.)

From sheath 11 the breathing gas is conveyed through a tube 13 provided with perforations 12 and out into the space between this tube 13 and the bladder 3 itself. The breathing gas is supplied continuously, and bladder 3 will thus always have an internal pressure which is substantially constant and which is prevented from reaching an impermissibly high value by means of a pressure limit valve which includes a one-way diaphragm 14 releasing breathing gas of impermissibly high pressure through outlet pipe 15. Said one-way diaphragm 14 may be actuated either if the supply of breathing gas increases too much or if the pressure in the lungs of the patient increases too much by breathing gas flowing from the inside of tube 13 through apertures 16 when the pressure of the breathing gas in tube 13 becomes so great that it displaces valve plate 14 against the action of a compression spring 17, one end of which engages said plate 14 and the other end of which engages a nut 18 guided in a longitudinal groove 19 in which a guide pin 20 can be displaced. The threads of said nut 18 engage the threads of a screw stem 21 which may be rotated by means of knob 22 so that spring 17 may be extended to a lesser or greater extent. The designation 23 refers to a lock ring which is locked in place by means of a blocking pin 24 in an annular groove 25.

Before valve block 6 illustrated in FIG. 3 is discussed additionally, pressure pulse generator 5 shown in FIG. 6 will be explained more in detail. The designation 4A refers to a conventional electronic pulse transmitter which is adjustable in such manner that it delivers pulses over leads 26 to a magnet valve 27, said pulses having a predetermined frequency corresponding to the intended breathing frequency of the patient. Air of comparatively high pressure is supplied through a feed line 28 to a high pressure regulator 29, the pressure of which is adjustable by means of an excentric disc 30 which is provided with a knob (not shown), with rotation of the excentric disc causing a change in the pressure of the output air from high pressure regulator 29. The emitted air is conveyed on one hand through a conduit 31 to an injector unit 32 and on the other hand through a conduit 33 to a low pressure regulator 34. Low pressure air is supplied from low pressure regulator 34 through conduit 35 to the interior of magnetic valve 27, and this supplied air is blocked when the valve plate 36 of the magnetic valve is retained in the position shown in the drawing through the action of a spring 38.

However, when magnetic valve 27 is actuated by receiving a pulse from pulse transmitter 4A through leads 26, magnetic plate 36 will be displaced to the left under the guidance of its stem 37 as the result of the influence of the pulse on a magnetic winding 38'. The opening of conduit 35 facing magnetic plate 36 will then be exposed, whereby air of comparatively low pressure flows out into the chamber 39 of the magnetic valve and continues through conduit 40 to the lower side of a spring-controlled roller diaphragm 41 which thus is urged upwardly. A needle valve 42 secured to roller diaphragm 41 is thereby lifted, which means that the high pressure air supplied to conduit 31 flows past the tip 43 of the needle valve and down through a primary injector nozzle 44 and a secondary injector nozzle 45, respectively, thereby carrying along atmospheric air through the apertures 32A down into the space between the above-mentioned inner casing 2 and the breathing bladder 3, i.e. into pressure chamber 46. Each time a pulse occurs in the electronic pulse transmitter 4A, the pressure chamber 46 will thus be set under pressure, with the breathing bladder 3 being squeezed together. When the pulse thereafter ceases, the pressure in pressure chamber 46 will immediately be relieved, as magnetic plate 36 then returns to its initial position and blocks leads 35, thereby causing a reduction of the pressure in chamber 39 as the result of a flow of fluid into channel 39' which was blocked by magnetic plate 36 when the latter was positioned in its actuated position. As the injector pressure towards pressure chamber 46 now ceases, the positive pressure in said pressure chamber will be conveyed out into the atmosphere through the secondary injector nozzle 75 and apertures 32A.

Returning now to FIG. 3 it becomes obvious that when breathing bladder 3 is squeezed together in the manner described above, breathing gas which is located in the interior of bladder 3 will be urged into sheath 13 through the perforations 12 and will actuate on one hand the above-mentioned one-way diaphragm 14 and on the other hand the check valve 47 which is actuated by a spring 48. This spring 48 is adjusted in such manner that valve plate 47 normally will open when bladder 3 is squeezed together, with breathing air being conveyed from the interior of the bladder, past check valve 47 (through openings 49 in the valve seat), and further on to the patient through a conduit 50.

Figure 5:
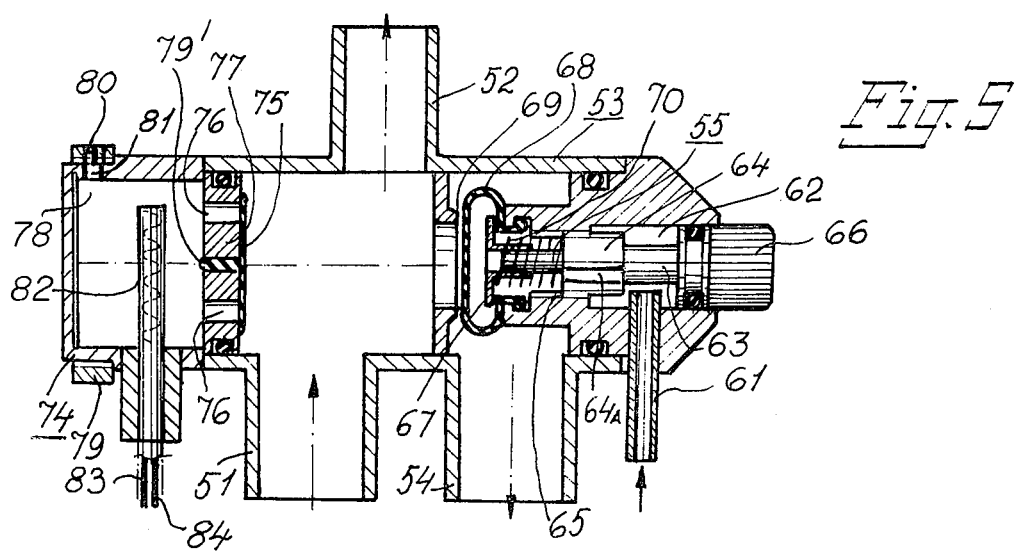
FIG. 5 is a sectional longitudinal view of a pilot valve included in the respirator system of the invention.

Conduit 50 is connected to the pipe 51 of FIG. 5, and the breathing gas is now conveyed in the direction of the arrow point in tubing 51 and further on in the direction of the arrow of pipe 52 to the lungs of the patient.

The control valve illustrated in FIG. 5 and generally designated 53 has the purpose of i.a. ensuring that breathing air supplied to the patient really reaches the latter and does not leak out through pipe 54. On the other hand the expiratory air of the patient is to be permitted to have full access to pipe 54 when expiration is to be performed. This control of the air is carried out by means of an expiratory valve 55 which operates in the following manner.

When valve block 6 is disposed in the position illustrated in FIG. 3 and breathing bladder 3 is squeezed together by means of a pressure applied in chamber 46 air will be urged from chamber 46 in the direction indicated by arrow 56 through a gap between a pin 58 and one of the walls 59 enclosing pressure chamber 46. This air is conveyed further through channel 60 and out through a tube 61. Tube 61 may be seen in FIG. 5, and the supplied air will thus flow into a chamber 62 in FIG. 5. Chamber 62 is provided with a stem 63 having a threaded portion 64 engaging a threaded portion 65 of the surrounding wall. As the result of this threaded engagement, rotation of knob 66 makes it possible to displace a valve plate 67 towards and away from, respectively, a bladder 68 consisting of appropriate material, for example silicone rubber. The air flowing through tube 61 is now conveyed into bladder 68 through a groove 64A and will thus urge bladder 68 against seat 69. By rotating knob 66 it now becomes possible to adjust the position of plate 67 so as to control the possibility of bladder 68 being urged away from valve seat 69 under the expiration phase. Therefore, this means that it becomes possible to control the work that the patient must perform when he is to breath out. The purpose of this is that a predetermined final-expiratory pressure is to be retained in the lungs. Around the stem on which valve plate 67 is disposed, there is also positioned a compression spring 70, whose purpose is to move plate 67 to the left when knob 66 is rotated in a predetermined direction and to ensure that plate 67 never can be urged rigidly against bladder 68 when the latter engages seat 69, as this could have fatal consequences to the patient. Thus, the patient is to be able to urge bladder 68 and plate 67 away, against the operation of spring 70, by means of the expiratory air.

In the description of the automatic valve 71 of FIG. 3 given above, the illustrated spring 72 has not been mentioned. The purpose of this spring is to engage component 94. FIG. 3 shows valve block 6 introduced into external casing 1 (compare FIG. 1), and therefore pin 57 is depressed. Thus, in this case all pumping activity towards the lungs of the patient will be carried out automatically under the actuation of the compressed air that is introduced into pressure chamber 46. However, it may be desirable to pump the air manually to make it possible to feel the reaction from the lungs of the patient in this manner. This may be performed by valve block 6 being rotated and removed from external casing 1. The coupling between these units may appropriately be performed by a bayonet catch of suitable type. When valve block 6 and the external casing 1 of the respirator have been separated, automatic valve 71 will be set to the position shown in FIG. 4. Pin 57 will then have been urged to the right by means of spring 72, which causes an annular groove 73 to form a connection between the interior of breathing bladder 3 and the openings 49 behind the check valve 47. By engaging the breathing bladder from the outside manually (the pressure of the breathing gas in the breathing bladder is substantially constant, as mentioned above) it will then become possible to manually pump air to the lungs of the patient through pipe 50. A pilot pressure will also in this case be supplied to the pilot valve in accordance with FIG. 5 through conduit 61, as the annular groove 73 communicates with channel 60 and thus with tube 61. However, it should be noted that in this case the pilot pressure will be derived from the interior of the breathing bladder 3.

The pilot valve of FIG. 5 contains additionally an important operative part, namely trigger valve 74, which, however, also may be separate with regard to the pilot valve. Trigger valve 74 comprises a one-way valve with a thin diaphragm 75, for example of silicon rubber, which diaphragm may be actuated if the patient shows a tendency to breath spontaneously, which may be observed as a weak suction towards the patient in pipe 52. Diaphragm 75 has a central stud 79' which retains it in a partition 77, but said weak suction may nevertheless be sufficiently strong for the periphery of diaphragm 75 to be displaced outwardly from its engagement with partition 77, whereby openings 76 towards the inner chamber 78 of valve 74 will become exposed. At one of its ends the wall around chamber 78 is surrounded by a rotatable ring 79 which is provided with a peripheral slot 80 which may be set in-position opposite to a greater or lesser number of bores 81 in the chamber wall. When the patient gasps, thereby displacing the periphery of diaphragm 75 from partition 77, a flow of air will thus be drawn through apertures 76 towards pipe 52, wherein the magnitude of this flow, although it is quite small, may be adjusted by ring 79 being rotated so that a greater or smaller number of apertures 81 become located opposite to the peripheral slot 80. When slot 80 is altogether open, the patient will always be completely exposed to the surrounding atmosphere.

Now, a hot-wire transmitter 82, which is extremely sensitive to temperature changes and which immediately is actuated if a flow of air moves through the chamber in the above-mentioned manner, is located in chamber 78. This actuation means that hot-wire transmitter 82 delivers over its leads 83 and 84 a pulse to the trigger cricuit 4B of FIG. 6. This trigger circuit will in turn release a pulse to magnetic valve 27 with the same effect that a pulse from pulse transmitter 4A has, i.e. quick reaction is achieved by the breathing bladder 3 being squeezed together by the action of compressed air introduced into chamber 46.

Figure 6:
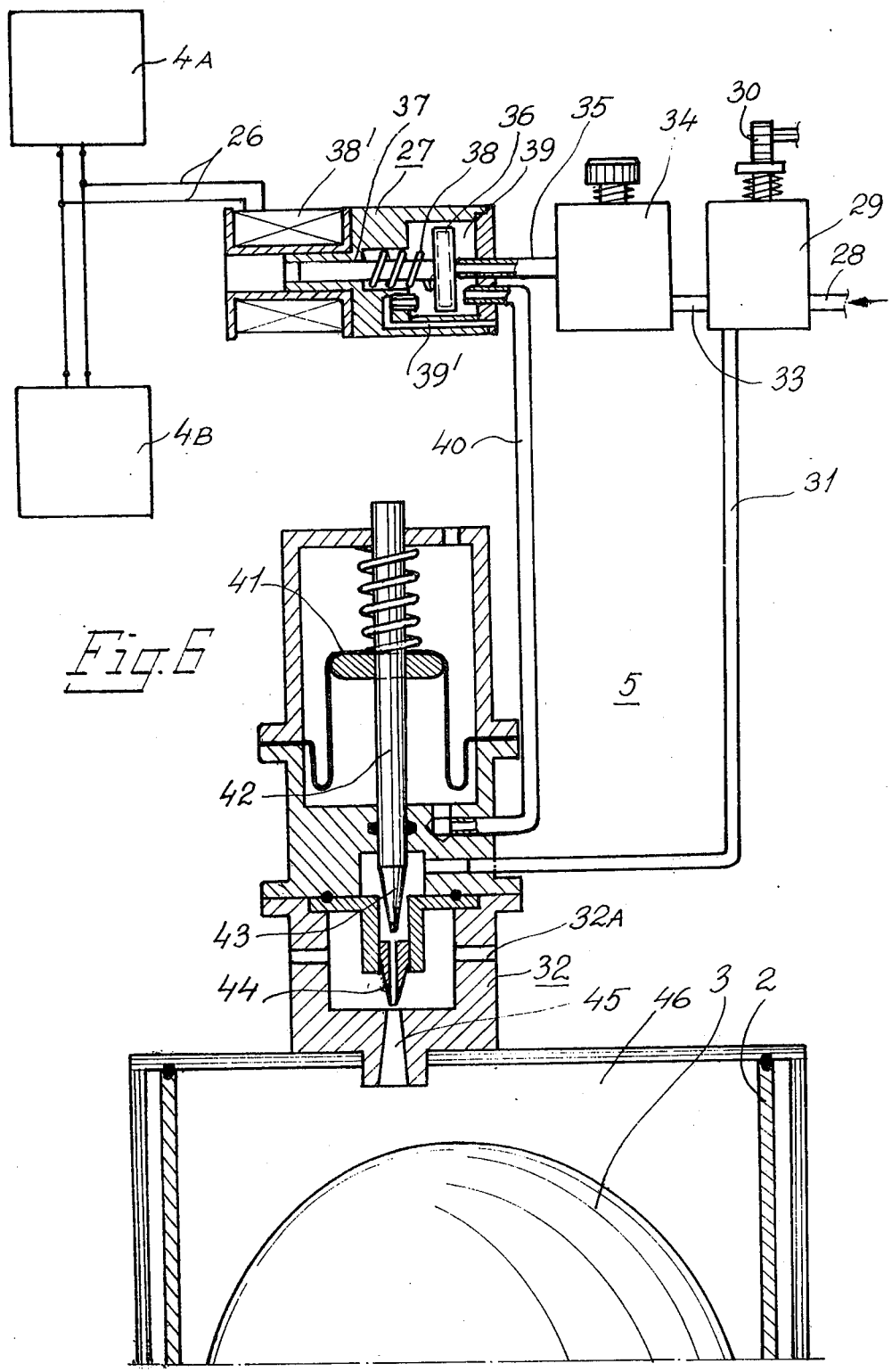
FIG. 6 illustrates diagrammatically a pressure pulse generator in accordance with the invention.

Trigger circuit 4B, which is diagrammatically shown as a block in FIG. 6, is illustrated more in detail in FIG. 7. As may be seen in FIG. 7, the leads 83 and 84 from the hot-wire transmitter are connected at the left side of the circuit. The circuit contains a number of resistors R1–R5 for providing appropriate bias voltages, furthermore an electrolytic capacitor C1, an amplifier 85, a comparator 86, and a transistor 87. The designation 27 refers to the same magnetic valve that is shown in FIG. 6. It is pointed out that the circuit illustrated in FIG. 6 only comprises an example of a electronic circuit which may be utilized in the relevant connection.

The invention is not restricted to the embodiment described above and illustrated in the drawings, and said embodiment merely comprises an example of the invention and of its utilization.

What is claimed is:

1. A respirator system comprising
   a. a pressure chamber,
   b. a breathing bladder,
   c. a pulse transmitter, d. a pressure pulse generator,
e. a valve block means,
f. a pilot valve,
g. an automatic valve means, and
h. an expiratory valve,
i. patient communication means,
wherein said breathing bladder contains breathing gas for substantially constant pressure and is disposed in said pressure chamber for being squeezed together and for expanding, respectively, as the result of the exterior of said breathing bladder intermittently being set under pressure of atmospheric air and being relieved, respectively, said pressure pulse generator being connected to said pressure chamber and being responsive to said pulse transmitter,
said valve block means being connected to said breathing bladder for supplying breathing gas to the interior of said bladder from a source of breathing gas and for discharging said gas from the interior of said bladder to said pilot valve, said patient communcation means being connected to said pilot valve,
said valve block means being detachably connected to the pressure chamber and including said automative valve means for connecting the pressure chamber to said pilot valve,
said pilot valve including said expiratory valve communication with said patient communication means, and
said automative valve means including spring-loaded pin means adapted for being depressed by said pressure chamber when said valve block is connected to said pressure chamber and including means for retaining open a pilot pressure channel supplied from said pressure chamber to said expiratory valve simultaneously with breathing gas being conveyed from the breathing bladder to one patient, whereas said pin means is extended when said valve block means is disconnected from said pressure chamber, thereby retaining the pilot pressure channel under pressure from the interior of the breathing bladder for simultaneously providing breathing gas to the patient by manual actuation of the breathing bladder.

2. A respirator system in accordance with claim 1, said system comprising a patient-triggered valve communicating with said patient communication means having an extremely easily movable diaphragm and a hot-wire transmitter means for actuating, as the result of a sudden spontaneous reaction of the patient, said pressure pulse transmitter substantially without any time delay so as to immediately place said pressure chamber under pressure, thereby causing breathing gas to be supplied to the lungs of the patient as the result of the pressure chamber pressure on the breathing bladder.

3. A respirator system in accordance with claim 2, wherein in addition to said expiratory valve the patient-triggered valve is also included as a portion of the pilot valve.

4. A respirator system in accordance with claim 3, wherein said expiratory valve includes a valve seat forming a port communicating with said patient communication means a valve bladder which when subjected to compressed gas from the pressure chamber or breathing gas from the breathing bladder engages said valve seat, said valve bladder being provided with means including a spring-loaded, displaceable pressure plate for cooperating with the valve bladder and the valve seat in such manner that a predetermined pressure is retained in the lungs of the patient after completed expiration.

5. A respirator system in accordance with claim 4, including an injector block having an injector means therein, said pressure pulse generator for supplying atmospheric air under comparatively high pressure being connected to said pressure chamber via said injector means, said injector block having openings therein communicating with said injector means whereby, said injector means communicates on one hand with said pressure chamber and on the other hand with the ambient atmosphere through said openings in said injector block so as to prevent a predetermined maximum pressure in the pressure chamber from being exceeded.

6. A respirator system in accordance with claim 5, wherein said pressure chamber is relieved of pressure by means of said openings.

7. A respirator system in accordance with claim 6, wherein the pressure chamber has a restricting wall which, in the longitudinal direction of the chamber, has oval cross-section.

* * * * *

UNITED STATES PATENT OFFICE
CERTIFICATE OF CORRECTION

Patent No. 4,014,326    Dated March 29, 1977

Inventor(s) Robert Muller

It is certified that error appears in the above-identified patent and that said Letters Patent are hereby corrected as shown below:

Col. 6, line 42 - "cricuit" s/b --circuit--

Col. 7, line 31 - "automative" s/b --automatic--

Col. 7, line 38 - "one" s/b --the--

Signed and Sealed this fifth Day of July 1977

[SEAL]

Attest:

RUTH C. MASON
Attesting Officer

C. MARSHALL DANN
Commissioner of Patents and Trademarks